United States Patent
Newburg et al.

(10) Patent No.: US 10,286,001 B2
(45) Date of Patent: *May 14, 2019

(54) USE OF PURIFIED 2'-FUCOSYLLACTOSE, 3-FUCOSYLLACTOSE AND LACTODIFUCOTETRAOSE AS PREBIOTICS

(71) Applicants: Glycosyn LLC, Woburn, MA (US); Trustees of Boston College, Chesnut Hill, MA (US)

(72) Inventors: David S. Newburg, Newtonville, MA (US); John M. McCoy, Reading, MA (US); Massimo Merighi, Somerville, MA (US); Matthew Ian Heidtman, Brighton, MA (US); Zhuoteng Yu, Brighton, MA (US)

(73) Assignees: Glycosyn LLC, Waltham, MA (US); Trustees of Boston College, Chesnut Hill, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/419,241

(22) Filed: Jan. 30, 2017

(65) Prior Publication Data

US 2017/0136049 A1    May 18, 2017

Related U.S. Application Data

(63) Continuation of application No. 13/469,499, filed on May 11, 2012, now Pat. No. 9,567,361.

(60) Provisional application No. 61/485,895, filed on May 13, 2011.

(51) Int. Cl.

| | | |
|---|---|---|
| A61K 31/702 | (2006.01) |
| C07H 3/06 | (2006.01) |
| A23L 33/00 | (2016.01) |
| A23L 33/21 | (2016.01) |
| A23L 33/28 | (2016.01) |
| A23L 33/10 | (2016.01) |
| A23L 2/52 | (2006.01) |

(52) U.S. Cl.
CPC .............. *A61K 31/702* (2013.01); *A23L 2/52* (2013.01); *A23L 33/10* (2016.08); *A23L 33/21* (2016.08); *A23L 33/28* (2016.08); *A23L 33/40* (2016.08); *C07H 3/06* (2013.01); *A23V 2002/00* (2013.01); *Y02A 50/473* (2018.01); *Y02A 50/481* (2018.01)

(58) Field of Classification Search
None
See application file for complete search history.

(56) References Cited

U.S. PATENT DOCUMENTS

| | | |
|---|---|---|
| 5,505,955 A | 4/1996 | Peterson et al. |
| 5,667,797 A | 9/1997 | Peterson et al. |
| 6,045,854 A | 4/2000 | Prieto et al. |
| 6,056,978 A * | 5/2000 | Beck ........... A61K 35/20 424/150.1 |
| 6,146,670 A | 11/2000 | Prieto et al. |
| 7,521,212 B1 | 4/2009 | Samain et al. |
| 7,893,041 B2 | 2/2011 | Morrow et al. |
| 8,197,872 B2 | 6/2012 | Mills et al. |
| 8,361,756 B2 | 1/2013 | Mills et al. |
| 8,425,930 B2 | 4/2013 | Barboza et al. |
| 8,999,705 B2 | 4/2015 | Mills et al. |
| 9,029,136 B2 | 5/2015 | Heidtman et al. |
| 9,200,091 B2 | 12/2015 | German et al. |
| 9,327,016 B2 | 5/2016 | Garrido et al. |
| 9,332,770 B2 | 5/2016 | Griffin et al. |
| 9,453,230 B2 | 9/2016 | Merighi et al. |
| 9,567,361 B2 | 2/2017 | Newburg et al. |
| 9,587,241 B2 | 3/2017 | Merighi et al. |
| 2002/0019991 A1 | 2/2002 | Prieto et al. |
| 2006/0014717 A1 | 1/2006 | Angstrom et al. |
| 2006/0122148 A1 | 6/2006 | Teneberg et al. |
| 2007/0275881 A1 | 11/2007 | Morrow et al. |
| 2009/0098240 A1 | 4/2009 | Mills et al. |
| 2009/0191551 A1 | 7/2009 | Morrow et al. |
| 2009/0197806 A1 | 8/2009 | Morrow et al. |
| 2010/0063002 A1 | 3/2010 | Stahl et al. |
| 2010/0113383 A1 | 5/2010 | Mills et al. |
| 2010/0120701 A1 | 5/2010 | McCoy et al. |
| 2010/0254949 A1 | 10/2010 | Barboza et al. |
| 2010/0260720 A1 | 10/2010 | Sprenger |
| 2010/0330040 A1 | 12/2010 | Knol et al. |
| 2012/0208181 A1 | 8/2012 | Merighi et al. |
| 2013/0011516 A1 | 1/2013 | Griffin et al. |
| 2013/0095528 A1 | 4/2013 | Mills et al. |
| 2013/0195803 A1 | 8/2013 | German et al. |
| 2014/0037785 A1 | 2/2014 | Barboza et al. |
| 2014/0080201 A1 | 3/2014 | Merighi et al. |
| 2015/0010670 A1 | 1/2015 | Mills et al. |

(Continued)

FOREIGN PATENT DOCUMENTS

| | | | | |
|---|---|---|---|---|
| EP | 2072052 | * | 6/2009 | ............ A61K 35/74 |
| JP | 2007525487 A | | 9/2007 | |

(Continued)

OTHER PUBLICATIONS

Wexler et al., Clin. Microbiol. Rev., 20(4):593-621 (2007).*
Adlard et al., Epidemiol. Infect., 121:237-241 (1998).*
Toruner et al., Gastroenterol., 134:929-936 (2008).*
Kunz et al., Bioactive Components of Milk, Z. Bosze (ed.) (2008).*
Gibson et al., Dietary modulation of the human colonic microbiota: introducing the concept of prebiotics. J Nutr. Jun. 1995;125(6):1401-12.
Kunz et al., Oligosaccharides in human milk: structural, functional, and metabolic aspects. Annu Rev Nutr. 2000;20:699-722.

(Continued)

*Primary Examiner* — Thomas J. Visone
(74) *Attorney, Agent, or Firm* — Mintz Levin Cohn Ferris Glovsky and Popeo, P.C.; Ingrid A. Beattie (57) ABSTRACT

The invention provides compositions and methods for utilizing synthetic human milk oligosaccharides as prebiotics.

23 Claims, 6 Drawing Sheets

(56) References Cited

U.S. PATENT DOCUMENTS

| | | |
|---|---|---|
| 2015/0044330 A1 | 2/2015 | Heidtman et al. |
| 2015/0110771 A1 | 4/2015 | Garrido et al. |
| 2016/0024543 A1 | 1/2016 | Merighi et al. |
| 2016/0143928 A1 | 5/2016 | German et al. |
| 2017/0081353 A1 | 3/2017 | McCoy et al. |
| 2017/0081689 A1 | 3/2017 | Heidtman et al. |

FOREIGN PATENT DOCUMENTS

| | | | |
|---|---|---|---|
| WO | WO-2005055944 A2 | 6/2005 | |
| WO | WO-2011008086 A1 | 1/2011 | |
| WO | WO-2011008087 A1 | 1/2011 | |
| WO | WO 2011/096808 * | 8/2011 | ............... A23L 1/29 |
| WO | WO-2015175801 A1 | 11/2015 | |
| WO | WO-2016040531 A1 | 3/2016 | |

OTHER PUBLICATIONS

Lee et al., Identification and screening for antimicrobial activity against Clostridium difficile of Bifidobacterium and Lactobacillus species isolated from healthy infant faeces. Int J Antimicrob Agents. Apr. 2003;21(4):340-6.

Newburg et al., Innate protection conferred by fucosylated oligosaccharides of human milk against diarrhea in breastfed infants. Glycobiology. Mar. 2004;14(3):253-63.

Roberfroid, M. Prebiotics: the concept revisited. J Nutr. Mar. 2007;137(3 Suppl 2):830S-7S.

Ashoor et al. (1983) "High performance liquid chromatographic determination of Bifidobacterium bifidum growth factors in human milk," J. Assoc. Off. Anal. Chem. 66(1)135-140.

Bakker-Zierikzee et al. (2005) "Effects of Infant Formula Containing a Mixture of Galacto- and Fructo-oligosaccharides or Viable Bifidobacterium Animalis on the Intestinal Microflora During the First 4 Months of Life," British Journal of Nutrition. 94:783-790.

Bezkorovainy et al. (1981) "Bifidobacterium bifidus var. Pennsylvanicus growth promoting activity of human milk casein and its derivatives," International Journal of Biochemistry. 13(5):585-590.

Bryant (Dec. 1, 1972) "Commentary on the Hungate Technique for Culture of Anaerobic Bacteria," The American Journal of Clinical Nutrition. 25(12):1324-1328.

Candela et al. (Sep. 2005) "Real-Time PCR Quantification of Bacterial Adhesion to Caco-2 Cells: Competition Between Bifidobacteria and Enteropathogens," Research in Microbiology. 156(8):887-895.

Caufield et al. (Jan. 1, 1993) "Initial Acquisition of Mutans Streptococci by Infants: Evidence for a Discrete Window of Infectivity," Journal of Dental Research. 72(1):37-45.

Charlwood et al. (1999) "A Detailed Analysis of Neutral and Acidic Carbohydrates in Human Milk," Analytical Biochemistry 273(2):261-277.

Chaturvedi et al. (2001) "Survival of Human Milk Oligosaccharides in the Intestine of Infants," Advances in Experimental Medicine and Biology. 501:315-323.

Chaturvedi et al. (Jun. 2001) "Fucosylated Human Milk Oligosaccharides Vary Between Individuals and Over the Course of Lactation," Glycobiology. 11(5):365-372.

Collado et al. (Oct. 2007) "Role of Commercial Probiotic Strains Against Human Pathogen Adhesion to Intestinal Mucus," Letters in Applied Microbiology. 45(4):454-460.

Cotter et al. (Oct. 2005) "Bacteriocins: Developing Innate Immunity for Food," Nature Reviews Microbiology. 3 (10):777-788.

Cummings et al. (May 2002) "Gastrointestinal Effects of Prebiotics," British Journal of Nutrition. 87(2):S145-S151.

Dominguez-Bello et al. (2008) "Do you have a Probiotic in Your Future?" Microbes and Infection. 10(9):1072-1076.

Dubert-Ferrandon et al. (2008) "Immune functions and mechanisms in the gastrointestinal tract," Handbook of Prebiotic 115-142.

György et al. (1974) "Undialyzable growth factors for Lactobacillus bifidus var. pennsylvanicus: protective effect of sialic acid bound to glycoproteins and oligosaccharides against bacterial degradation," European Journal of Biochemistry. 43(1):29-33.

Hamosh (Feb. 2001) "Bioactive Factors in Human Milk," Pediatric Clinics of North America. 48(1):69-86.

Hopkins et al. (2005) "Characterisation of Intestinal Bacteria in Infant Stools Using Real-Time PCR and Northern Hybridisation Analyses," FEMS Microbiology Ecology. 54(1):77-85.

Hughes et al. (Jun. 1, 2008) "In Vitro Fermentation of Oat and Barley Derived Beta-Glucans by Human Faecal Microbiota," FEMS Microbiology Ecology. 64(3):482-493.

Krausova et al. (2015) "Impact of purified human milk oligosaccharides as a sole carbon source on the growth of lactobacilli in in vitro model," African Journal of Microbiology Research. 9(9):565-571.

Locascio et al. (2007) "Glycoprofiling of bifidobacterial consumption of human milk oligosaccharides demonstrates strain specific, preferential consumption of small chain glycans secreted in early human lactation," Journal of Agricultural and Food Chemistry. 55(22):8914-8919.

Locascio et al. (2010) "Comparative genomic hybridization of Bifidobacterium longum strains reveals broad conservation of milk utilization genes in subsp. infantis," Applied and Environmental Microbiology. 1-33.

Marcobal et al. (2010) "Consumption of human milk oligosaccharides by gut-related microbes," J Agric Food Chem. 58:5334-5340.

Martín-Sosa et al. (Jan. 2003) "Sialyloligosaccharides in Human and Bovine Milk and in Infant Formulas: Variations with the Progression of Lactation," Journal of Dairy Science. 86(1):52-59.

Menard et al. (Jan. 21, 2008) "Developmental Switch of Intestinal Antimicrobial Peptide Expression," The Journal of Experimental Medicine. 205(1):183-193.

Morrow et al. (Sep. 2004) "Human Milk Oligosaccharides are Associated with Protection Against Diarrhea in Breast-Fed Infants," The Journal of Pediatrics. 145(3):297-303.

Newburg (Feb. 2001) "Bioactive Components of Human Milk: Evolution, Efficiency, and Protection," Advances in Experimental Medicine and Biology. 501(1):3-10.

Newburg (Mar. 1999) "Human Milk Glycoconjugates that Inhibit Pathogens," Current Medicinal Chemistry. 6 (2):117-127.

Newburg et al. (1998) "Role of Human-Milk Lactadherin in Protection Against Symptomatic Rotavirus Infection," The Lancet 351(9110):1160-1164.

Newburg et al. (2005) "Human milk glycans protect infants against enteric pathogens," Annu Rev Nutr. 25:37-58.

Newburg et al. (2007) "Protection of the neonate by the innate immune system of developing gut and of human milk," Pediatr Res. 61:2-8.

Nichols et al. (1974) "Human colostral whey MI glycoproteins and their L. bifidus var. Penn. growth promoting activities," Life Sciences. 14(5):967-976.

Nichols et al. (1975) "Isolation and characterization of several glycoproteins from human colostrum whey," Biochimica et Biophysica Acta (BBA)—Protein Structure. 412(1):99-108.

Ninonuevo et al. (Oct. 4, 2006) "A Strategy for Annotating the Human Milk Glycome," Journal of Agricultural and Food Chemistry. 54(20):7471-7480.

Parkkinen et al. (1987) "Isolation of Sialyl Oligosaccharides and Sialyl Oligosaccharide Phosphates from Bovine Colostrum and Human Urine," Methods in Enzymology. 138:289-300.

Rockova et al. (2012) "Inter-species differences in the growth of bifidobacteria cultured on human milk oligosaccharides," Folia Microbiologica. 57(4):321-324.

Sakamoto et al. (2006) "Reclassification of Bacteroides distasonis, Bacteroides goldsteinii and Bacteroides merdae as Parabacteroides distasonis gen. nov., comb. nov., Parabacteroides goldsteinii comb. nov. and Parabacteroides merdae comb. nov," International Journal of Systematic and Evolutionary Microbiology. 56(7):1599-1605.

Schwiertz et al. (2003) "Development of the Intestinal Bacterial Composition in Hospitalized Preterm Infants in Comparison with Breast-Fed, Full-Term Infants," Pediatric Research. 54(3):393-399.

(56) References Cited

OTHER PUBLICATIONS

Sela et al. (2011) "An infant-associated bacterial commensal utilizes breast milk sialyloligosaccharides," Journal of Biological Chemistry. 1-29.
Servin (Feb. 2004) "Antagonistic Activities of Lactobacilli and Bifidobacteria Against Microbial Pathogens," FEMS Microbiology Reviews. 28:405-440.
Shen et al. (Jul. 6, 2001) "Resolution of Structural Isomers of Sialylated Oligosaccharides by Capillary Electrophoresis," Journal of Chromatography A. 921(2):315-321.
Tissier (1905) "Repartition des microbes dans l'intestin du nourisson," Ann Inst Pasteur. 19:109-123.
Vanderpool et al. (2008) "Mechanisms of Probiotic Action: Implications for Therapeutic Applications in Inflammatory Bowel Diseases," Inflammatory Bowel Disease. 14(11):1585-1596.
Ward et al. (2007) "In Vitro Fermentability of Human Milk Oligosaccharides by Several Strains of Bifidobacteria," Molecular Nutrition & Food Research. 51(11):1398-1405.
Ward et al. (Jun. 2006) "In Vitro Fermentation of Breast Milk Oligosaccharides by Bifidobacterium infantis and Lactobacillus gasseri," Applied and Environmental Microbiology. 72(6):4497-4499.
Wexler (Oct. 2007) "Bacteroides: the Good, the Bad, and the Nitty-Gritty," Clinical Microbiology Reviews. 20(4):593-621.
Williams (2010) "Probiotics," American Journal of Health-System Pharmacy. 67(6):449-458.
Yu et al. (2012) "The principal fucosylated oligosaccharides of human milk exhibit prebiotic properties on cultured infant microbiota," Glycobiology. 23(2):169-177.
Yu et al. (2013) "Utilization of major fucosylated and sialylated human milk oligosaccharides by isolated human gut microbes," Glycobiology. 23(11):1281-1292.
Zhang et al. (Feb. 2009) "Development of Chemically Defined Media Supporting High-Cell-Density Growth of Lactococci, Enterococci, and Streptococci," Applied and Environmental Microbiology. 75(4):1080-1087.

\* cited by examiner

USE OF PURIFIED 2'-FUCOSYLLACTOSE, 3-FUCOSYLLACTOSE AND LACTODIFUCOTETRAOSE AS PREBIOTICS

RELATED APPLICATIONS

This application is a continuation of U.S. application Ser. No. 13/469,499, now U.S. Pat. No. 9,567,361, filed May 11, 2012, which claims the benefit of priority under 35 U.S.C. § 119(e) to U.S. Provisional Application No. 61/485,895, filed May 13, 2011, the contents of each of which are incorporated herein by reference in their entireties.

STATEMENT AS TO FEDERALLY SPONSORED RESEARCH

This invention was made with Government Support under Contract Number NIAID U01A1075563 by the National Institutes of Health. The Government has certain rights in the invention.

FIELD OF THE INVENTION

The invention provides compositions and methods for utilizing oligosaccharides as prebiotics, in particular certain fucosylated oligosaccharides that are typically found in human milk.

BACKGROUND OF THE INVENTION

Human milk contains a diverse and abundant set of neutral and acidic oligosaccharides. Although these molecules may not be utilized directly for nutrition, they nevertheless serve critical roles in the prevention of disease, in immune function, and in the establishment of a healthy gut microbiome. The bacteria present in the human intestine are critically associated with human health, and an abnormal/pathogenic intestinal microflora can be detrimental to host survival.

SUMMARY OF THE INVENTION

To maximize the beneficial effect of endogenous commensal or symbiotic microbes or exogenously-administered probiotics, prebiotic agents are administered to stimulate the growth and/or activity of advantageous/symbiotic bacteria in the digestive system. As such, there is a pressing need to develop new prebiotic agents that selectively improve the survival and effectiveness of beneficial/symbiotic microbes. The invention is based on the discovery that fucosylated human milk oligosaccharides in a highly purified form, e.g., 2'-fucosyllactose (2'-FL), 3-fucosyllactose (3-FL), or lactodifucotetraose (LDFT), are useful as prebiotic compositions. The prebiotic compositions described herein are indigestible or partially indigestible (by the host), but provide health benefits to the host by promoting the growth of certain probiotic microorganisms. The compositions preferentially promote growth of probiotic bacteria compared to pathogenic microorganisms. Thus, the invention provides prebiotic compositions comprising purified human milk oligosaccharides (HMOS) in an amount effective to stimulate the growth of endogenous commensal or symbiotic microbes or exogenously administered probiotics. Preferably, the oligosaccharide composition comprises purified 2'-fucosyllactose (2'-FL), purified 3-fucosyllactose (3-FL), purified lactodifucotetraose (LDFT), or combinations thereof. A combination of purified 2'-FL and purified 3-FL synergistically stimulates the growth and/or activity of advantageous/symbiotic bacteria in the digestive system. Optionally, purified LDFT is added to this combination. Preferably, the 2'-FL, 3-FL, or LDFT is 95-99% pure. The prebiotic oligosaccharides of the invention are administered alone (i.e., in the absence of exogenously administered bacteria). Alternatively, the prebiotic oligosaccharides of the invention are administered in conjunction with live microorganisms (i.e., probiotics). The composition optionally includes a pharmaceutically-acceptable excipient or inactive ingredients.

As used herein, an "isolated" or "purified" oligosaccharide is substantially free of other oligosaccharides, with which it naturally occurs in human milk. Purified oligosaccharides are also free of cellular material when produced biosynthetically, or other chemicals when chemically synthesized. Purified compounds are at least 60% (by dry weight) of the compound of interest. Preferably, the preparation is at least 75%, more preferably at least 90%, and most preferably at least 99%, by weight the compound of interest. For example, a purified oligosaccharide, e.g., 2'-FL, 3-FL, or LDFT is one that is at least 90%, 91%, 92%, 93%, 94%, 95%, 98%, 99%, or 100% (w/w) of the desired oligosaccharide by weight. Purity is measured by any appropriate standard method, for example, by column chromatography, thin layer chromatography, or high-performance liquid chromatography (HPLC) analysis. The oligosaccharides are purified and used in a number of products for consumption by humans as well as animals, such as companion animals (dogs, cats) as well as livestock (bovine, equine, ovine, caprine, or porcine animals, as well as poultry). "Purified" also defines a degree of sterility that is safe for administration to a human subject, e.g., lacking infectious or toxic agents.

Similarly, by "substantially pure" is meant an oligosaccharide that has been separated from the components that naturally accompany it. Typically, the oligosaccharide is substantially pure when it is at least 60%, 70%, 80%, 90%, 95%, or even 99%, by weight, free from the proteins and naturally-occurring organic molecules with which it is naturally associated.

The prebiotic compositions described herein stimulate the growth of endogenous commensal or symbiotic microbes or exogenously administered probiotics of various genera including *Bifidobacterium*, *Lactobacillus*, or *Streptococcus*. *Saccharomyces boulardii* is a suitable probiotic yeast. Suitable probiotic bacteria include *Bacillus coagulans* (e.g. *Bacillus coagulans* GBI-30 or 6086), *Bacteroides fragilis*, *Bacteroides thetaiotaomicron*, *Bifidobacterium animalis* (e.g. *Bifidobacterium animalis* BB-12), *Bifidobacterium breve*, *Bifidobacterium bifidum* (e.g. *Bifidobacterium bifidum* BB-12), *Bifidobacterium infantis* (e.g. *Bifidobacterium infantis* 35624), *Bifidobacterium lactis*, *Bifidobacterium longum*, *Escherichia coli*, *Enterococcus faecalis*, *Enterococcus faecium*, *Lactobacillus acidophilus* (e.g. *Lactobacillus acidophilus* RC-14, NCFM or CL 1285), *Lactobacillus casei* (e.g. *Lactobacillus casei* LBC8OR), *Lactobacillus fermentum* (e.g. *Lactobacillus fermentum* B-54), *Lactobacillus paracasei* (e.g. *Lactobacillus paracasei* NCC2461 or 8700: 2), *Lactobacillus johnsonii* (e.g. *Lactobacillus johnsonii* NCC533), *Lactococcus lactis*, *Lactobacillus plantarum* (e.g. *Lactobacillus plantarum* 299v or HEAL 9), *Lactobacillus reuteri* (e.g. *Lactobacillus reuteri* SD2112 or DSM 17938), *Lactobacillus rhamnosus* (e.g. *Lactobacillus rhamnosus* GG or GR-1), and *Streptococcus thermophilus*. Preferably, the probiotic bacteria are selected from the group consisting of *Bifidobacterium bifidum*, *Bacteroides fragilis*, *Bacteroides thetaiotaomicron*, *Bifidobacterium infantis*, *Bifidobacterium*

*longum, Lactobacillus acidophilus, Lactobacillus rhamnosus* and *Streptococcus thermophilus*.

The prebiotic composition comprises between 0.01 g oligosaccharide, e.g., 2'-FL, 3-FL, or LDFT, and 10 g oligosaccharide per 10 grams of composition. For example, the prebiotic composition comprises between 0.1 g and 5 g 2'-FL, between 0.5 g and 5 g 2'-FL, between 1 g and 5 g 2'-FL, or between 1.5 g and 3 g 2'-FL per 10 grams of composition. Alternatively, the 2'-FL comprises 90% to 100% by weight of the composition, e.g., 92% to 100%, 95% to 100%, 96% to 100%, 97% to 100%, 98% to 100%, or 99% to 100% by weight of the composition.

The mean concentrations of 2'-FL, 3-FL, and LDFT in human milk are as follows: 2'-FL=2.43g/L (±0.26), 3-FL=0.86g/L (±0.10), and LDFT=0.43g/L (±0.04; Chaturvedi P, et al. 2001 Glycobiology, May;11(5):365-72). Thus, the mean ratio of 2'-FL:3FL:LDFT in human milk is 5.65:2:1. The prebiotics of the invention are administered in any ratio of 2'-FL:3FL:LDFT, e.g., 1:1:1, 5:2:1, 10:5:1, 1:2:5, 1:5:10, 5:1:2, 10:1:5, 2:1:5, or 5:1:10, or any other ratio suitable to obtain prebiotic effects. Alternatively, 2'-FL and 3-FL are administered together in the following exemplary ratios of 2'-FL:3-FL 1:1, 1:2, 1:5, 1:10, 1:100, 100:1, 10:1, 5:1, or 2:1.

The composition is in the form of a tablet, a capsule, a powder, a beverage, or an infant formula. For example, the purified prebiotic oligosaccharides of the invention are in the form of powdered/dry milk. By "infant" is meant a child under the age of 12 months. By "infant formula" is meant a foodstuff intended for particular nutritional use by infants aged under twelve months and constituting the principal liquid element in the progressively diversified diet of this category of person. Alternatively, the composition is provided in mashed rice, in a banana, in a porridge, or in a gruel. Due to the surge in disease in infants at weaning, the HMOS of the invention are added to weaning foods (e.g., mashed rice, bananas, porridges and other gruels, formula, etc.) to reduce or ameliorate these diseases. Optionally, the HMOS are added to the weaning foods during the manufacturing process. Alternatively, the synthetic HMOS are added to the weaning foods after the manufacturing process, but prior to ingestion. For example, packets of sugars including one or more purified HMOS are added to weaning foods prior to infant ingestion. In one aspect, the composition further comprises probiotic bacteria, which are prevented from premature utilization of the prebiotic component through physical means (e.g. separation by a physical barrier) or through other means (e.g. through reversible metabolic stasis of the probiotic organism, e.g. as provided by desiccation or refrigeration). In another aspect, the composition further comprises fructo-oligosaccharides (FOS), galacto-oligosaccharides (GOS), or lactulose.

The purified 2'-FL, 3-FL, or LDFT prebiotic oligosaccharide is also added to other consumable products such as yogurt or probiotic beverages for consumption by infants, children, and adults. For example, the purified 2'-FL, 3-FL, or LDFT prebiotic oligosaccharide is added to powdered/dry milk.

Also provided are methods of stimulating the growth of endogenous commensal or symbiotic microbes or exogenously administered probiotics in the gastrointestinal tract by administering to the gastrointestinal tract of a subject a composition comprising an effective amount of purified human milk oligosaccharides (HMOS). Preferably, the HMOS comprises purified 2'-fucosyllactose (2'-FL), purified 3-fucosyllactose (3-FL), purified lactodifucotetraose (LDFT), or a combination thereof. A combination of purified 2'-FL, purified 3-FL, and purified lactodifucotetraose (LDFT) synergistically stimulates the growth and/or activity of advantageous/symbiotic bacteria in the digestive system. Also provided is the use of purified 2'-FL, purified 3-FL, and/or purified LDFT in the manufacture of a medicament for stimulating the growth of bacteria in the gastrointestinal tract. Preferably, the 2'-FL, 3-FL, or LDFT is 95-99% pure. The composition comprises between 0.01 g 2'-FL and 10 g 2'-FL per 10 grams of composition, e.g., between 0.1 g and 5 g 2'-FL, between 0.5 g and 5 g 2'-FL, between 1 g and 5 g 2'-FL, or between 1.5 g and 3 g 2'-FL per gram of composition. Alternatively, the 2'-FL comprises 90% to 100% by weight of the composition, e.g., 92% to 100%, 95% to 100%, 96% to 100%, 97% to 100%, 98% to 100%, or 99% to 100% by weight of the composition.

Administration of the purified prebiotics described herein improves the overall health of the gastrointestinal tract by influencing many members of the microbial community. The prebiotics described herein activate signaling pathways within the intestinal mucosa, inhibit pathogen binding to mucosal surfaces, and attenuate inflammation of the intestinal mucosa. For example, administration of the purified prebiotics of the invention results in a decrease in infection by enteric pathogens, a decrease in diarrhea, a decrease in constipation, a reduction in toxic catabolites, a reduction of intestinal cancer, and an enhanced immune response. In one example, the subject is a mammal in need of treatment, e.g., a subject that has been diagnosed with infectious diarrhea, acute infectious diarrhea, antibiotic-associated diarrhea (AAD), traveler's diarrhea (TD), necrotizing enterocolitis (NEC), inflammatory bowel disease, Helicobacter pylori infection, respiratory tract infection, ear, nose, or throat (ENT) infection, or an infectious complication in surgical and critically ill patients. The mammal can be, e.g., any mammal, e.g., a human, a primate, a mouse, a rat, a dog, a cat, a horse, as well as livestock or animals grown for food consumption, e.g., cattle, sheep, pigs, chickens, and goats. In a preferred embodiment, the mammal is a human.

The local pH in the gastrointestinal tract is decreased following administration of the compositions of the invention. Additionally, the local lactate or lactic acid concentration in the gastrointestinal tract is increased following administration of the compositions of the invention. Finally, the growth of pathogenic bacteria in the gastrointestinal tract is inhibited following administration of the compositions of the invention.

In one example, the endogenous commensal or symbiotic microbes or exogenously administered probiotics stimulated by the compositions of the invention are selected from the group consisting of *Bifidobacterium bifidum, Bacteroides fragilis, Bacteroides thetaiotaomicron, Bifidobacterium infantis, Bifidobacterium longum, Lactobacillus acidophilus, Lactobacillus rhamnosus, Bacteroides vulgatus, Lactococcus lactis,* and *Streptococcus thermophilus*. Alternatively, the compositions of the invention stimulate the probiotic yeast *Saccharomyces boulardii*.

In one aspect, the administered composition further comprises probiotic bacteria selected from the group consisting of *Bifidobacterium bifidum, Bacteroides fragilis, Bacteroides thetaiotaomicron, Bifidobacterium infantis, Bifidobacterium longum, Lactobacillus acidophilus, Lactobacillus rhamnosus, Bacteroides vulgatus, Lactococcus lactis,* and *Streptococcus thermophilus*. In another aspect, the composition further comprises fructo-oligosaccharides (FOS), galacto-oligosaccharides (GOS), or lactulose. Preferably, the pathogenic bacteria is selected from the group consisting of *Clostridium histolyticum, Clostridium difficile,*

*Clostridium perfringens, Enterobacter aerogenes, Listeria monocytogenes, Staphylococcus aureus, Salmonella enterica, Yersinia enterocolitica*, enteropathogenic *Escherichia coli* (EPEC), enteroinvasive *Escherichia coli* (EIEC), enteroaggregative *Escherichia coli* (EAEC), enterotoxigenic *Escherichia coli*, enterohemorrhagic *Escherichia coli* (EHEC), e.g., *Escherichia coli* O157:H7, *Escherichia coli* O111:H8, *Escherichia coli* O104:H21, *Escherichia coli* O26:H11, *Escherichia coli* O103:H2, *Escherichia coli* O111:NM, and *Escherichia coli* O113:H21.

The terms "treating" and "treatment" as used herein refer to the administration of an agent or formulation to a clinically symptomatic individual afflicted with an adverse condition, disorder, or disease, so as to effect a reduction in severity and/or frequency of symptoms, eliminate the symptoms and/or their underlying cause, and/or facilitate improvement or remediation of damage. The terms "preventing" and "prevention" refer to the administration of an agent or composition to a clinically asymptomatic individual who is susceptible to a particular adverse condition, disorder, or disease, and thus relates to the prevention of the occurrence of symptoms and/or their underlying cause.

By the terms "effective amount" and "therapeutically effective amount" of a formulation or formulation component is meant a sufficient amount of the formulation or component to provide the desired effect. For example, by "an effective amount" is meant an amount of an oligosaccharide to increase the proliferation of endogenous commensal or symbiotic microbes or exogenously administered probiotics or prolong the residence time of the bacteria in the gastrointestinal tract of a subject who has consumed the bacteria. Ultimately, the attending physician or veterinarian decides the appropriate amount and dosage regimen.

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

Other features and advantages of the invention will be apparent from the following description of the preferred embodiments thereof, and from the claims. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, Genbank/NCBI accession numbers, and other references mentioned herein are incorporated by reference in their entirety. In the case of conflict, the present specification, including definitions, will control. In addition, the materials, methods, and examples are illustrative only and not intended to be limiting.

DETAILED DESCRIPTION

The human intestinal microflora is largely stable when the host is in good health; however, the ecosystem of the intestinal microflora varies depending on host age, disease, microorganism infection, stress, nutritional components, and pharmaceutical treatments. Modification of the composition and metabolic activity of the intestinal bacterial community, which can confer a health benefit to the host, may be achieved by administration of growth promoting sugars (i.e. prebiotics), by administration of live exogenous microorganisms (i.e., probiotics), or a combination of both.

Described herein are compositions that contain one or more highly purified prebiotic fucosylated oligosaccharides, e.g., 2'-fucosyllactose (2'-FL), 3-fucosyllactose (3-FL), and lactodifucotetraose (LDFT), in amounts that promote proliferation and residence of endogenous commensal or symbiotic microbes or exogenously administered probiotics in the mammalian gut. One or a combination of purified human milk oligosaccharides (HMOS) described herein alter microbiota composition in human stools, and stimulate the growth of beneficial/symbiotic bacteria in the human intestine. Certain bacteria present in the human intestine are associated with human health, and an abnormal/pathogenic intestinal microflora can be detrimental to host survival. The human intestinal microflora is largely stable when the host is in good health; however, the ecosystem of the intestinal microflora may change depending on host age, disease, microorganism infection, stress, nutritional components, and pharmaceutical administration.

Modification of the composition and metabolic activity of the intestinal bacterial community is performed through the administration of prebiotic oligosaccharides alone (i.e., in the absence of exogenously administered bacteria), beneficial microorganisms (i.e., probiotics), or a combination of prebiotics and probiotics. As described in detail below, to maximize the beneficial effect of endogenous commensal microbes or exogenously administered probiotic microorganisms, prebiotic agents (purified oligosaccharides) are administered to stimulate the growth and/or activity of advantageous bacteria in the digestive system. Described herein are prebiotic agents that selectively improve the survival and effectiveness of probiotic microbes. For example, as described in detail below, isolated and/or purified 2'-FL, 3-FL, or LDFT are administered to selectively stimulate the growth of beneficial bacteria.

The Human Microbiome

Mammals appear to be born free of bacteria, fungi, or protozoa; however, exposed organs—skin, body invaginations, and digestive tract—become niches for adapted microbes. These mucosal surfaces serve as the body's interaction with the external environment. The contents of these organs are kept separated from the "interior" of the body by barriers that effectively cordon the luminal microbes. Humans have a developmental program for expression of antimicrobial peptides modulating the microbial ecosystem that begins to form shortly after birth (Menard S, et al. 2008 J Exp Med, 21; 205(1): 183-193). The process of colonization is dynamic, creating the structured populations reached in the ultimate community, which itself is subject to perturbations (Caufield P W, et al. 1993 J. Dent Res, 72(1):37-45; Schwiertz A, et al. 2003 Pediatr Res, 54(3):393-399; Hopkins M J, et al. 2005 FEMS Microbiology Ecology, 54(1): 77-85). The choreography of such events is modulated by the complex interactions involving microbial signaling with other microbes and with the host.

The relationship between gut flora and humans is not merely commensal (a non-harmful coexistence), but rather a symbiotic relationship. Though people can survive without gut flora, the microorganisms perform a variety of useful functions, such as fermenting unused energy substrates, training the immune system, preventing growth of pathogenic bacteria, regulating the development of the gut, producing vitamins for the host (such as biotin and vitamin K), and producing hormones to direct the host to store fats (See, e.g., Dominguez-Bello M G and Blaser M J, 2008 Microbes Infect, 10(9): 1072-1076). However, in certain conditions, pathogenic species are capable of causing disease by producing infection or increasing cancer risk for the host.

Infant Gut Microbiota

The sterile gastrointestinal tract of the newborn is inoculated with microflora from the birth canal, close maternal contact, and the environment. Initial colonization is followed by waves of succession. Post-natal development, intrinsically modulated by both genetic and microbial factors, leads to a functionally healthy intestine that maintains a dynamic balance between microbes, host epithelial cells, and mucosal immunity. The initial pioneering species include facultative anaerobes such as lactobacilli and bifidobacteria, which initially establish the acidic anaerobic environment in which the increasingly complex microbiota is established over time. Exclusive breastfeeding promotes a human milk-induced intestinal predominance of *Bifidobacterium bifidum* (1,000:1 ratio of bifidobacteria to enterobacteria) and other favorable strains of bacteria that acidify the gut (stool pH of 5.1 by 7 days), which favors further colonization by the same symbiotic anaerobes (bifidobacteria and lactobacilli). A secondary wave of succession is noted at around 4 months by the increasing presence of *Bacteroides* spp, including *Bacteroides fragilis* and *Bacteroides thetaiotaomicron*, which eventually become dominant species in the adult microflora.

Probiotic Bacteria

The term "probiotic" is derived from a Greek word meaning "supporting or favoring life" (See, e.g., Vanderpool C, et al. 2008 Inflamm Bowel Dis, 14(11):1585-96). Probiotics are often in the form of dietary supplements containing beneficial bacteria or yeasts. The World Health Organization characterizes probiotics as "live microorganisms which when administered in adequate amounts confer a health benefit on the host" (Report of a Joint FAO/WHO Expert Consultation on Evaluation of Health and Nutritional Properties of Probiotics in Food Including Powder Milk with Live Lactic Acid Bacteria (October 2001)). Probiotics are often derived from healthy human microflora, and reduce the risk of disease upon ingestion. Common probiotics include *Bifidobacterium* and *Lactobacillus* species, *Streptococcus thermophilus, Enterococcus* and *Bacillus* species, *E. coli*, and yeasts such as *Sacharomyces boulardii*. The consumption of probiotics reduces diarrhea, necrotizing enterocolitis (NEC), inflammatory bowel diseases, and allergic disease. Probiotics protect high-risk infants from NEC by "normalizing" the abnormal bowel colonization of premature infants by providing an increased barrier to translocation of bacteria across the gut mucosa, by competitive exclusion of potential pathogens, and by growth inhibition of bacterial pathogens. Premature infants are poorly colonized by beneficial *Bifidobacterium*, and very low birth weight infants fed probiotic combinations of *Bifidobacterium infantis* and *Lactobacillus acidophilus*, or *Bifidobacterium infantis, Streptococcus thermophilus*, and *Bifidobacterium bifidus* have lower incidence and severity of NEC, and less death, compared with controls.

Probiotics exert direct antibacterial effects on pathogens through production of antibacterial substances, including bacteriocins and acid (Cotter P D, et al. 2005 Nat Rev, 3:777-788; Servin A L, 2004 FEMS Microbiol Rev, 28: 405-440). These probiotic-derived antibacterial substances exert their effects alone or synergistically to inhibit the growth of pathogens. Specifically, probiotic bacteria, especially strains of lactobacilli, produce acetic, lactic, and propionic acid that lower the local pH, which inhibits the growth of a wide range of Gram-negative pathogenic bacteria. Probiotics administered to the gastrointestinal tract also decrease adhesion of both pathogens and their toxins to the intestinal epithelium. Several strains of beneficial bacteria, including lactobacilli and bifidobacteria are able to compete with pathogenic bacteria, including *Clostridium histolyticum, Clostridium difficile, Enterobacter aerogenes, Listeria monocytogenes, Staphylococcus aureus, Salmonella enterica, Yersinia enterocolitica*, enterotoxigenic *E. coli*, and enteropathogenic *E. coli* for intestinal epithelial cell binding. Moreover, probiotic bacteria displace pathogenic bacteria even if the pathogens have attached to intestinal epithelial cells prior to probiotic administration (Collado M C, et al. 2007 Lett Appl Microbiol, 45: 454-460; Candela M, et al. 2005 Res Microbiol, 156: 887-895). Specific probiotics or probiotic combinations are selected based on their ability to inhibit or displace a specific pathogen.

Both in vitro and in vivo studies show effects of probiotics on host immune functions and intestinal epithelial cell functions (See, e.g., Vanderpool C, et al. 2008 Inflamm Bowel Dis, 4(11):1585-96). Probiotic-induced upregulation of immune function improves the ability to fight infections or inhibit tumor formation, while downregulation prevents the onset of allergy or intestinal inflammation. Probiotic bacteria stimulate intestinal epithelial cell responses, including restitution of damaged epithelial barrier, production of antibacterial substances and cell-protective proteins, and blockade of cytokine-induced intestinal epithelial cell apoptosis. Many of these responses result from probiotic stimulation of specific intracellular signaling pathways in the intestinal epithelial cells.

Human Milk Glycans

Human milk contains a diverse and abundant set of neutral and acidic oligosaccharides. For example, the prebiotic fucosylated oligosaccharides described herein, e.g., 2'-fucosyllactose (2'-FL), 3-fucosyllactose (3-FL), and lactodifucotetraose (LDFT), are typically found in human milk. Human milk oligosaccharides as a class survive transit through the intestine of infants very efficiently, being essentially indigestible (Chaturvedi, P et al. 2001 Adv Exp Med Biol, 501:315-323). Although these molecules may not be utilized directly by infants for nutrition, they nevertheless serve critical roles in the establishment of a healthy gut microbiome (Marcobal A, et al. 2010 J Agric Food Chem, 58:5334-5340), in the prevention of disease (Newburg D, et al. 2005 Annu Rev Nutr, 25:37-58), and in immune function (Newburg D, et al. 2007 Pediatr Res, 61: 2-8). Despite millions of years of exposure to human milk oligosaccharides (HMOS), pathogens have yet to develop ways to circumvent the ability of HMOS to prevent adhesion to target cells and to inhibit infection. The ability to utilize HMOS as pathogen adherence inhibitors promises to address the current crisis of burgeoning antibiotic resistance. Human milk oligosaccharides represent the lead compounds of a novel class of therapeutics against some of the most intractable scourges of society.

Human milk glycans, which comprise both unbound oligosaccharides and their glycoconjugates, play a significant role in the protection and development of the infant gastrointestinal (GI) tract. Milk oligosaccharides found in various mammals differ greatly, and composition in humans is unique (Hamosh M, 2001 Pediatr Clin North Am, 48:69-86; Newburg D, 2001 Adv Exp Med Biol, 501:3-10). Moreover, glycan levels in human milk change throughout lactation and also vary widely among individuals (Morrow A et al., 2004 J Pediatr, 145:297-303; Chaturvedi P et al., 2001 Glycobiology, 11:365-372). Approximately 200 distinct human milk oligosaccharides have been identified and combinations of simple epitopes are responsible for this diversity (Newburg D, 1999 Curr Med Chem, 6:117-127; Ninonuevo M et al., 2006 J Agric Food Chem, 54:7471-74801). Human milk oligosaccharides are composed of 5 monosaccharides: D-glucose (Glc), D-galactose (Gal), N-acetylglucosamine (GlcNAc), L-fucose (Fuc), and sialic acid (N-acetyl neuraminic acid, NeuSAc, NANA). Human milk oligosaccharides are usually divided into two groups according to their chemical structures: neutral compounds containing Glc, Gal, GlcNAc, and Fuc, linked to a lactose (Galβ1-4G1c) core, and acidic compounds including the same sugars, and often the same core structures, plus NANA (Charlwood J, et al. 1999 Anal Biochem, 273:261-277; Martin-Sosa, et al. 2003 J Dairy Sci, 86:52-59; Parkkinen J and Finne J, 1987 Methods Enzymol, 138:289-300; Shen Z, et al. 2001 J Chromatogr A, 921:315-321).

Approximately 70-80% of oligosaccharides in human milk, e.g., 2'-fucosyllactose (2'-FL) and 3-fucosyllactose (3-FL), lactodifucotetraose (LDFT), are fucosylated. Secretor fucosylglycans in human milk and secretor fucosylated epitopes in the infant gut select for microbiota that interact with fucose. These microbiota promote healthy colonization, and thereby reduce infections and inflammatory diseases of the gastrointestinal tract.

Human milk glycans have structural homology to cell receptors for enteropathogens and function as receptor decoys. For example, pathogenic strains of Campylobacter bind specifically to glycans containing H-2, i.e., 2'-fucosyl-N-acetyllactosamine or 2'-fucosyllactose (2'-FL). Campylobacter binding and infectivity are inhibited by 2'-FL and other glycans containing this H-2 epitope. Similarly, some diarrheagenic E. coli pathogens are strongly inhibited in vivo by human milk oligosaccharides containing 2-linked fucose moieties. Several major strains of human caliciviruses, especially the noroviruses, also bind to 2-linked fucosylated glycans, and this binding is inhibited by human milk 2-linked fucosylated glycans. Consumption of human milk that has high levels of these 2-linked fucosyloligosaccharides was associated with lower risk of norovirus, Campylobacter, ST of E. coli-associated diarrhea, and moderate-to-severe diarrhea of all causes in a Mexican cohort of breastfeeding children (Newburg D et al., 2004 Glycobiology, 14:253-263; Newburg D et al., 1998 Lancet, 351:1160-1164).

Human Milk Glycans as Prebiotics

Human milk contains a complex oligosaccharide mixture with prebiotic characteristics. As described herein, human milk oligosaccharides such as 2'-fucosyllactose (2'-FL), 3-fucosyllactose (3-FL), and lactodifucotetraose (LDFT) have prebiotic properties and are administered individually or in combination to stimulate the growth of specific beneficial bacteria that modulate mucosal immunity and confer protection against pathogens in newborns. Prebiotic oligosaccharides are short-chain carbohydrates with a degree of polymerization between 2 and 60, and are indigestible by human or animal digestive systems. The defining property of prebiotics is their ability to selectively stimulate the growth of beneficial bacteria including bifidobacteria and lactobacilli in the large intestine (Cummings J H and Macfarlane G T, 2002 Br J Nutr, 87(suppl 2):S145-S151). The prebiotic oligosaccharides are fermented by the gut flora, resulting in the release of hydrogen and carbon dioxide gas and short-chain fatty acids such as butyrate. The short-chain fatty acids reduce the pH of the stools, which leads to a mild laxative effect with softening and increased frequency of stools. Thus, prebiotics, including the purified 2'-FL, 3-FL and ,LDFT described herein prevent the constipation that is frequently observed in formula-fed infants. In addition, the acidic pH prevents growth of pathogens, promotes robust growth of healthy organisms, and promotes integrity of colonic epithelial cells.

Prebiotics encourage selective changes in both the composition and activity of the gastrointestinal microbiota, thereby conferring many health benefits upon the host, including the reduction of enteric and other diseases. Prebiotics stimulate the growth of the beneficial bacteria including bifidobacteria, the genus often predominant in the intestinal microbiota of breast-fed infants. The prebiotic HMOS described herein arrive undigested in the distal gut and act as substrates for fermentation.

As described herein, human milk glycans function as prebiotic agents that stimulate beneficial colonization of the infant gut. For example, in 1905, a unique predominance of lactobacilli, particularly Lactobacillus bifidus (now classified as Bifidobacterium bifidum) was noted in the microflora of breastfed infants. In 1953, a 'bifidus factor' was isolated from human milk that specifically stimulated growth of this bacterium. The milk factor was characterized in 1974 as a glycan containing N-acetylglucosamine, galactose, glucose, fucose, and sialic acid; however, sialic acid removal did not reduce activity. The amount of growth-promoting glycan activity varied widely among milk from different individuals. Bovine milk and infant formula contained an order of magnitude less 'bifidus' activity than human milk.

As described herein, ingestion of specific purified human milk glycans, e.g., 2'-fucosyllactose (2'-FL), 3-fucosyllactose (3-FL) and lactodifucotetraose (LDFT) cause specific beneficial bacteria/symbionts to dominate the infant microbiome. This is associated with positive consequences to the microbial ecosystem of the neonatal gut and subsequent health of the child. However, the prebiotic HMOS described herein are not limited to use in human infants. The prebiotic HMOS of the invention are administered to an infant or adult mammal. The mammal can be, e.g., any mammal, e.g., a human, a primate, a mouse, a rat, a dog, a cat, a horse, as well as livestock or animals grown for food consumption, e.g., cattle, sheep, pigs, chickens, and goats. Preferably, the mammal is a human Prior to the invention described herein, the addition of mixtures of fructo-oligosaccharides (FOS) and galacto-oligosaccharides (GOS) to infant formula stimulated colonization by B. bifidum and several lactobacilli (See also, Bakker-Zierikzee A, et al. 2005 British Journal of Nutrition, 94, 783-790). Described in detail below is the ability of milk glycans, such as 2'-fucosyllactose (2'-FL), 3-fucosyllactose (3-FL) and lactodifucotetraose (LDFT) to promote colonization by beneficial microbes. Although bacteria have been isolated from the human microbiome that utilize human milk oligosaccharides (Marcobal A, et al. 2010 J Agric Food Chem, 58(9): 5334-5340; Ward RE, et al. 2006 Appl Environ Microbiol, 72(6): 4497-4499; Ward R E, et al. 2007 Mol Nutr Food Res, 51(11): 1398-1405), prior to the invention described herein, the prebiotic effect of individual, purified human milk oligosaccharides, either native or synthetic, was unknown.

Purified human milk oligosaccharides 2'-FL (MW=488), 3-FL (MW=488) and LDFT (MW=635) are utilized as prebiotics to promote the proliferation and residence of beneficial bacteria in the human intestine. As described in detail below, the prebiotic effects of human milk oligosaccharides including 2'-fucosyllactose were analyzed on the microbial community of infants, and on individual microbes isolated from human microbiota known to utilize human milk oligosaccharides. The testing was performed on anaerobic cultures of these communities and isolates of the microbiota.

Secretor Human Milk Glycans and Secretor Infant Gut Glycans Promote Colonization by Secretor-Binding Microbiota Secretor fucosylglycans in human milk and secretor fucosylated epitopes in the infant gut select for microbiota that interact with fucose. These microbiota promote healthy colonization, and thereby reduce infections and inflammatory diseases of the gastrointestinal tract. The bifidus factor described above is only one minor component of HMOS. As described below, the fucosyloligosaccharides represent approximately 85% of the human milk glycome, and also stimulate the growth of specific microbes to produce a beneficial pattern of microbiota. Fucosylated glycans are also prevalent on the mucosal cell surface as the gut matures. Common members of the human microbiota, including *Bacteroides fragilis, Bacteroides thetaiotaomicron*, and *Roseburia inulinivorans*, utilize fucose during their colonization of the intestine. As described above, these three phenomena are related, and constitute an integrated system for introduction of specific types of microbes into the intestinal microbial community.

Expression of glycans in the intestine changes over the course of infant development, and glycan content in human milk changes over the course of lactation. These systems work synergistically to direct microbial succession of the gut microbiota toward the more complex pattern seen in adults. Gut glycan expression varies among individuals in relation to their histo-blood group types, and expression of fucosyl glycans in milk reflects variation in maternal Lewis histo-blood group type. Thus, in the gastrointestinal (GI) tract of the breastfeeding infant, variation in glycans provided by milk and variation in the glycans expressed on infant mucosal surface combine to produce specific glycan patterns that support specific combinations of microbiota. These patterns and degrees of microbiota colonization are determinants of specific outcomes, including risk of necrotizing enterocolitis.

As described in detail below, the plant prebiotic fructooligosaccharide stimulated growth, reduced pH, and induced the production of lactic acid in fecal slurrys containing the human microbiome and individual bacteria that are part of the human microbiome. Human milk oligosaccharides (HMOS) also exhibit these prebiotic traits. As described below, individual pure, synthetic HMOS 2'-FL, 3-FL and LDFT promote bacterial growth, decrease pH, and induce the production of lactic acid. Prior to the invention described herein, purified 2'-FL, 3-FL and LDFT were not individually characterized as prebiotic compounds. As described below, prebiotic agents such as 2'-FL, 3-FL and LDFT are associated with many health benefits, including decreased enteric and other infectious diseases, decreased constipation, increased calcium absorption, and decreased risk of inflammatory disease.

Due to the surge in disease in infants at weaning, the HMOS of the invention are added to weaning foods (e.g., mashed rice, bananas, porridges and other gruels, formula, etc.) to reduce or ameliorate these diseases. Optionally, the HMOS are added to the weaning foods during the manufacturing process. Alternatively, the synthetic HMOS are added to the weaning foods after the manufacturing process, but prior to ingestion. For example, packets of sugars including HMOS are added to weaning foods prior to infant ingestion.

EXAMPLE 1

2'-fucosyllactose (2'-FL), 3-fucosyllactose (3-FL) and lactodifucotetraose (LDFT) are Prebiotic Agents The hypothesis that human milk oligosaccharides as a group, and that the individual human milk oligosaccharides 2'-fucosyllactosel, 3-fucosyllactose and lactodifucotetraose are prebiotic was tested directly on mixed microbial communities derived from infant feces, and on purified microbial strains isolated from human microbiota. Testing was performed on anaerobic cultures of these communities and isolates of the microbiota.

First, the impact of 2'-FL and HMO were examined on fresh samples of mixed microbiota of three infants. A carbohydrate-free basal medium was prepared according to Hughes (Hughes S, et al. 2008 FEMS Microbiol Ecol, 64(3): 482-93) to study the growth of fecal bacteria during fermentation of human milk oligosaccharides (HMO) or 2'-FL. This basal medium contained per liter: 2 g peptone (Oxoid Ltd., Basingstoke, UK), 2 g yeast extract (Oxoid), 0.1 g NaCl, 0.04 g $K_2HPO_4$, 0.01 g $MgSO_4.7H_2O$, 0.01 g $CaCl_2.6H_2O$, 2 g $NaHCO_3$, 0.005 g haemin (Sigma), 0.5 g L-cysteine HCl (Sigma), 0.5 g bile salts (Oxoid), 2 ml Tween 80, 10 µl vitamin K (Sigma), and 4 ml of 0.025% (w/v) resazurin solution. Anaerobic culture methods were those described in Bryant (Bryant, M 1972 Am J Clin Nutr, 25(12): 1324-8) using Hungate culture tubes, sealed with butyl rubber septa. Media were prepared and maintained anaerobically using $O_2$-free $CO_2$.

Figure 1:
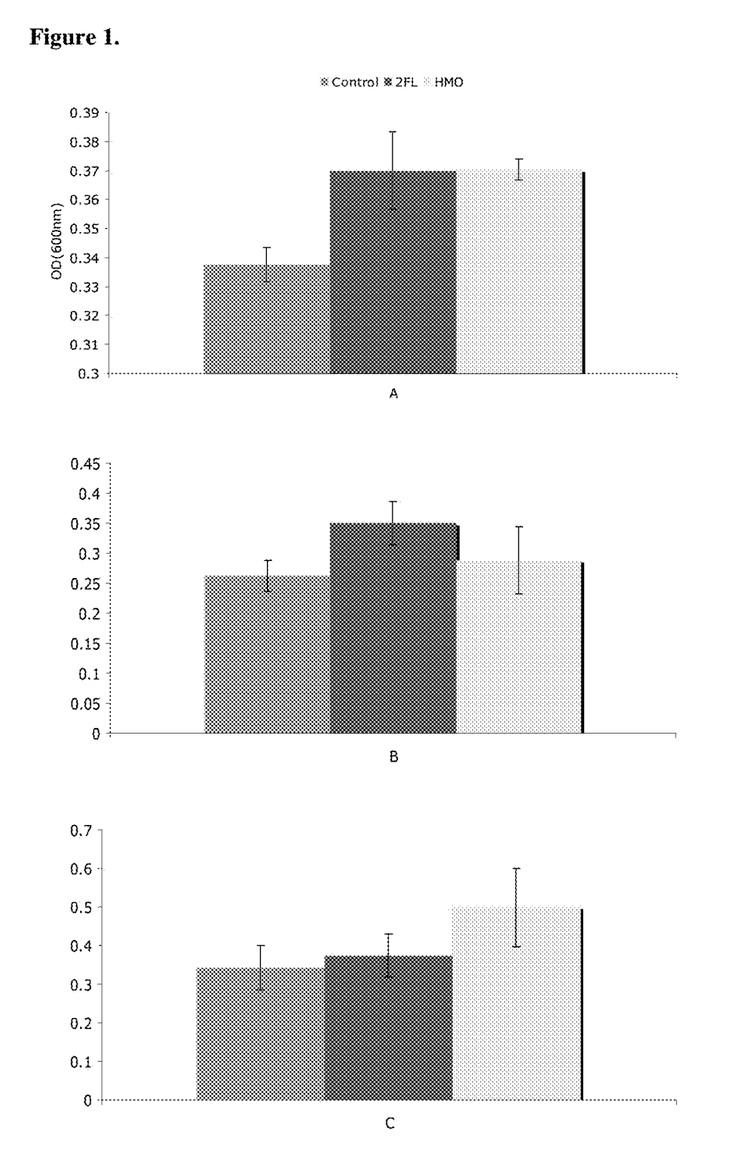
FIG. 1 is a series of bar charts demonstrating that 2'-fucosyllactose (2'-FL) and human milk oligosaccharides (HMO) induce bacterial growth in infant microbiota cultures from three healthy babies, identified as A, B, and C.
Figure 2:
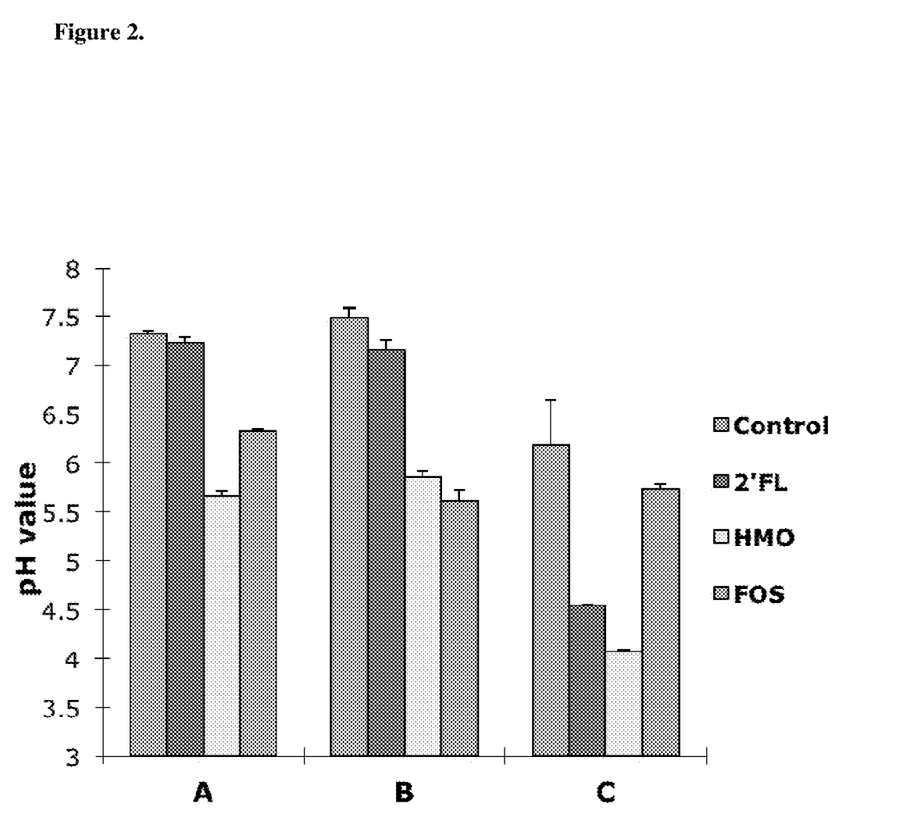
FIG. 2 is a bar chart demonstrating that 2'-FL and HMO decrease pH in infant microbiota cultures from three healthy babies, identified as A, B, and C.
Figure 3:
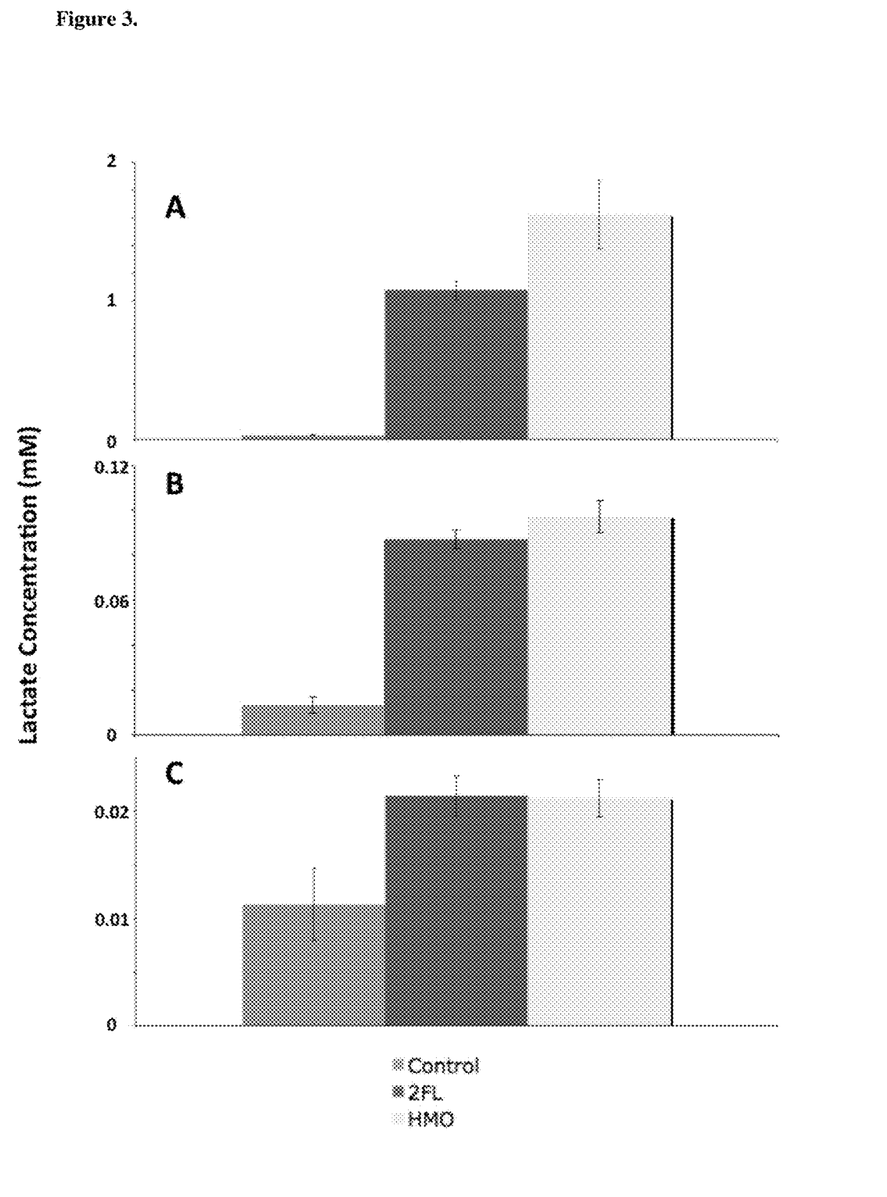
FIG. 3 is a series of bar charts demonstrating that 2'-FL and HMO increase lactate concentration in infant microbiota cultures from three healthy babies, identified as A, B, and C.

Fresh fecal samples were collected from three healthy babies, identified as A, B and C, who had not received antibiotics or pre/probiotics and had no history of gastrointestinal disorder. Fresh human infant feces were added to phosphate-buffered sterile anaerobic saline solution (1:10 feces to saline), mixed in a blender for 60 s, homogenized and filtered through a double layer of sterile cheesecloth. 2 g/L 2'FL and 5 g/L HMO were dissolved for 1 hour in medium before inoculation with 10% (v/v) fecal slurry prepared as above. Hungate tubes containing 2'-FL or HMO were inoculated with fecal material, serving as the treatment. Hungate tubes containing no substrate were also inoculated with feces, to serve as negative control. All tubes were incubated at 37° C. Culture supernatant samples were taken at 24 h. All samples were stored at −20° C. for further analysis. FIGS. 1, 2 and 3 show the results. Prebiotics are associated with an increase in the numbers of microbiota, especially bifidobacteria and lactobacilli, a decrease in gut pH, and an increase in lactic acid. FIG. 1 demonstrates that both 2'-FL at 2 g/L and HMOS at 5 g/L induced an increase in total bacteria in microbiota derived from the fecal slurry of 3 individual infants after culture in vitro. FIG. 2 demonstrates that pH is reduced in each of these three microbial communities after growth in the presence of 2'-FL or HMOS. Also, when these three microbial communities are each cultured in the presence of 2'-FL or HMOS, significantly higher amounts of lactic acid are produced compared to controls (FIG. 3). These changes are all characteristic of prebiotics.

Next, the responses to human milk oligosaccharides of a number of purifed bacterial strains that had mainly been isolated from human (infant) feces were examined. Individual bacterial isolates (mostly bifidobacteria and a few bacteroidetes) were tested in the presence or absence of 2'-FL at 2 g/L, 3-FL at 2 g/L, LDFT at 2 g/L and HMOS at 5 g/L, approximating the average concentrations of these sugars in human milk. FOS (fructooligosaccharide, a prototypic plant prebiotic) at 2 g/L was also tested (approximating the concentrations of FOS used in infant formulae). Bacterial strain isolates (Table 1) were obtained from the Japanese Collection of Microorganism (RIKEN BioResource Center, Japan), and the American Type Culture Collection (Manassas, Va.).

TABLE 1

| Species | Origin |
|---|---|
| *Bifidobacterium longum* JCM 7007 | Feces of human infant |
| *Bifidobacterium longum* JCM 7009 | Feces of human infant |
| *Bifidobacterium longum* JCM 7010 | Feces of human infant |
| *Bifidobacterium longum* JCM 7011 | Feces of human infant |
| *Bifidobacterium longum* JCM 1210 | Feces of human infant |
| *Bifidobacterium longum* JCM 1260 | Feces of human infant |
| *Bifidobacterium longum* JCM 1272 | Feces of human infant |
| *Bifidobacterium longum* JCM 11347 | Feces of human infant |
| *Bifidobacterium longum* ATCC 15708 | Feces of human infant |
| *Bifidobacterium longum* ATCC 15697 | Feces of human infant |
| *Bacteroides vulgatus* ATCC 8482 | n/a |
| *Bacteroides fragilis* ATCC 25285 | Appendix abscess |
| *Clostridium perfringens* ATCC 13124 | n/a |
| *Escherichia coli* ATCC 35401 | Human feces |

For these experiments a chemically defined medium (ZMB1) containing amino acids but no carbohydrates, and which supports the growth of many enteric bacteria was used (Zhang, G., Mills, D. A., and Block, D. E. (2009) *Appl Environ Microbiol* 75, 1080-1087). For the individual strain growth experiments, ZMB1 media supplemented with either 2g/L 2'-FL, 2 g/L 3-FL, 2 g/L LDFT or 5 g/L HMO were prepared. Each bacterial culture was then innoculated to 0.5 OD (600 nm) at the outset. ZMB1 cultures containing no additional oligosaccharide substrate served as negative controls., while ZMB1 cultures containing 2 g/L FOS served as positive controls. All bacteria were grown in anaerobic conditions at 37° C., using an anaerobic chamber (DG250 Anaerobic Workstation, Don Whitley Scientific Limited, West Yorkshire, UK). Culture supernatant samples were taken at 48 h. Growth was assessed by optical density (OD 600 nm) in a microtiter plate. Culture pH was also recorded after 48 h of growth. Lactic acid concentrations in the cultures at the end of fermentation were assayed using a lactate assay kit (kit no.K607-100; BioVision Inc., CA, USA). All experiments were carried out in quadruplicate.

Figure 4:
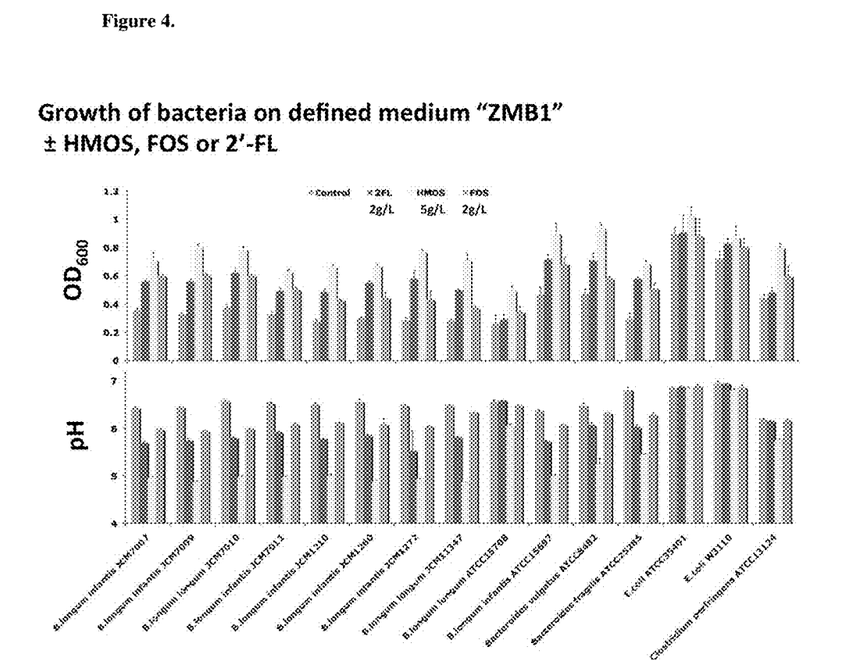
FIG. 4 is a series of bar charts demonstrating the effect of 2'-FL, human milk oligosaccharides (HMOS), and fructo-oligosaccharides (FOS) on the growth (optical density (OD)) and final culture pH of various bacteria.
Figure 5:
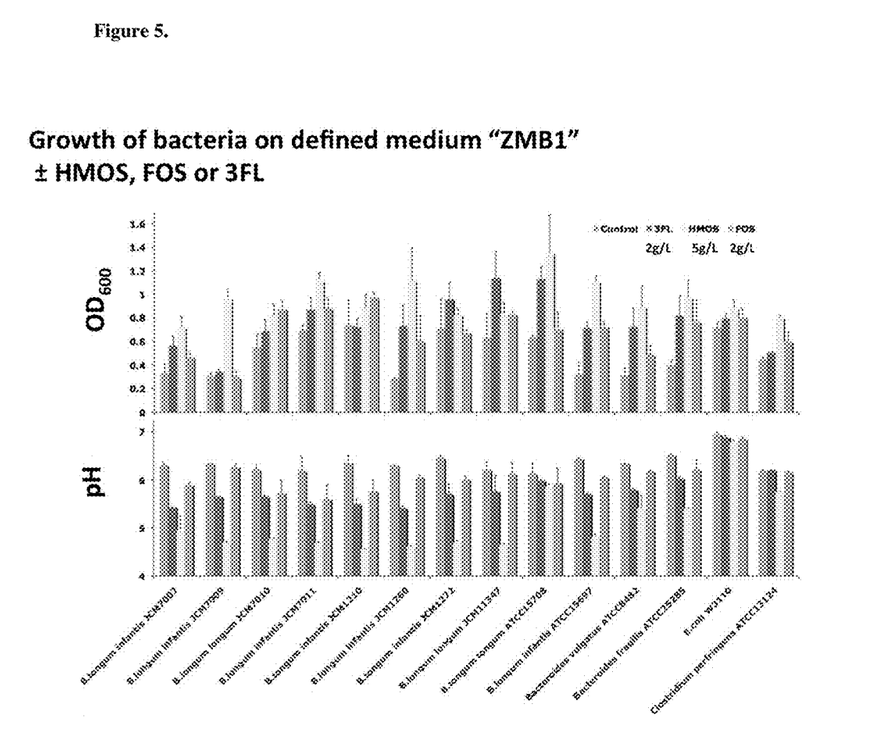
FIG. 5 is a series of bar charts demonstrating the effect of 3-FL, human milk oligosaccharides (HMOS), and fructo-oligosaccharides (FOS) on the growth (optical density (OD)) and final culture pH of various bacteria.
Figure 6:
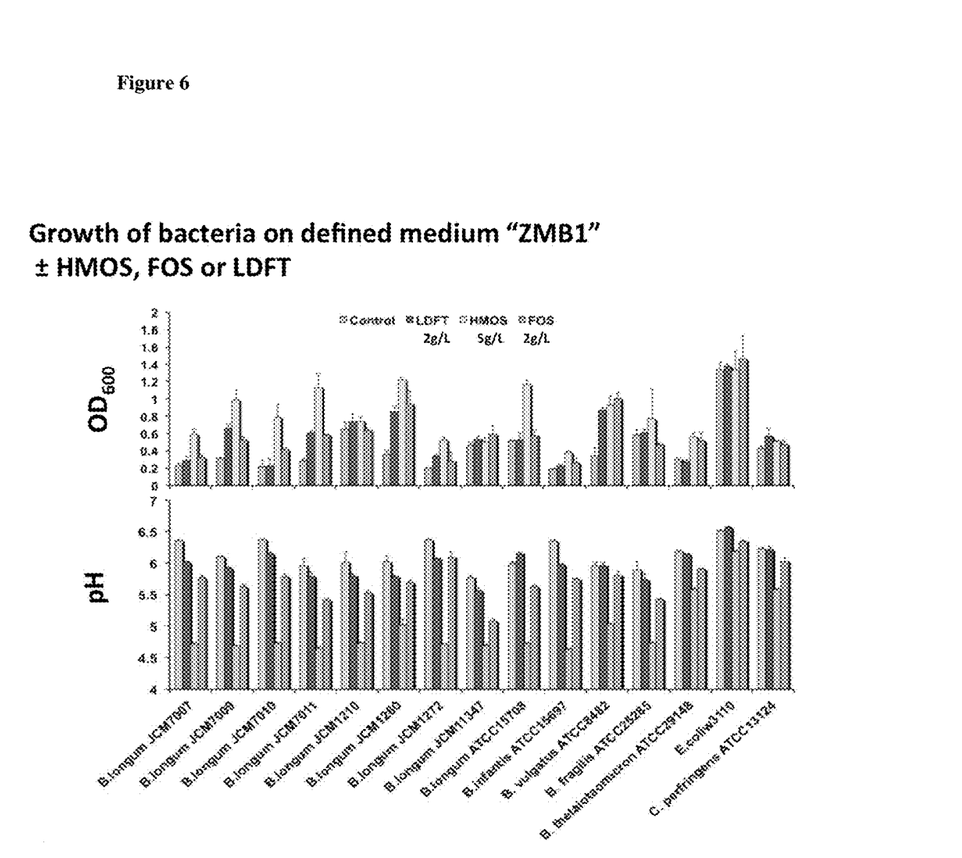
FIG. 6 is a series of bar charts demonstrating the effect of LDFT, human milk oligosaccharides (HMOS), and fructo-oligosaccharides (FOS) on the growth (optical density (OD)) and final culture pH of various bacteria.

For most of these bacteria, growth was stimulated (to various degrees) by 2'-FL, 3-FL, LDFT, HMOS or FOS, and the pH of cultures decreased (FIGS. 4 and 5). In most cases the decrease in pH was as at least as great for 2'-FL, 3-FL and LDFT as for FOS, which is an exemplar oligosaccharide with prebiotic activity. These data indicate that purified 2'-FL, 3-FL and LDFT each can function as a highly potent prebiotic independent of other HMOS components.

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. Genbank and NCBI submissions indicated by accession number cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

What is claimed:

1. A method for stimulating the growth of an exogenously administered probiotic bacterium in a gastrointestinal tract of a mammalian subject, comprising:
   administering to said subject a composition comprising an oligosaccharide, wherein said oligosaccharide consists of (a) purified 2'-fucosyllactose (2'-FL), (b) purified 3-fucosyllactose (3-FL), (c) purified lactodifucotetraose (LDFT), or (d) a combination thereof, wherein the composition further comprises a probiotic *Bacteroides* sp. bacterium, wherein said oligosaccharide selectively stimulates the growth of said probiotic *Bacteroides* sp. bacterium, and wherein the *Bacteroides* sp. bacterium is a *Bacteroides fragilis, Bacteroides thetaiotaomicron*, or *Bacteroides vulgatus* bacterium.

2. The method of claim 1, wherein said 2'-FL, said 3-FL, or said LDFT is at least 90%, 95%, 98%, or 99% pure.

3. The method of claim 1, wherein the local pH in said gastrointestinal tract is decreased following administration of said composition.

4. The method of claim 1, wherein the local lactate or lactic acid concentration in said gastrointestinal tract is increased following administration of said composition.

5. The method of claim 1, wherein the growth of a pathogenic bacterium in said gastrointestinal tract is inhibited following administration of said composition.

6. The method of claim 5, wherein said pathogenic bacterium is selected from the group consisting of *Clostridium histolyticum, Clostridium difficile, Clostridium perfringens, Enterobacter aerogenes, Listeria monocytogenes, Staphylococcus aureus, Salmonella enterica, Yersinia enterocolitica*, enterotoxigenic *E. coli*, and enteropathogenic *E. coli*.

7. The method of claim 6, wherein said pathogenic bacterium is selected from the group consisting of *Enterobacter aerogenes, Listeria monocytogenes, Staphylococcus aureus, Salmonella enterica*, and *Yersinia enterocolitica*.

8. The method of claim 1, wherein said composition comprises between 0.01 g 2' FL and 1g 2'-FL per gram of composition.

9. The method of claim 1, wherein said subject is an infant.

10. The method of claim 1, wherein said composition is in the form of an infant formula.

11. The method of claim 1, wherein said composition is provided in dry milk, in mashed rice, in a banana, in a porridge, or in a gruel.

12. A method for stimulating the growth of an exogenously administered probiotic bacterium in a gastrointestinal tract of a mammalian subject, comprising:
    administering to said subject a composition comprising (a) purified 2'-fucosyllactose (2'-FL), (b) purified 3-fucosyllactose (3-FL), (c) purified lactodifucotetraose (LDFT), or (d) a combination thereof, wherein said subject comprises an exogenously administered probiotic *Bacteroides* sp. bacterium, wherein said composition stimulates the growth of said exogenously administered probiotic *Bacteroides* sp. bacterium, and wherein the *Bacteroides* sp. bacterium is a *Bacteroides fragilis, Bacteroides thetaiotaomicron*, or *Bacteroides vulgatus* bacterium.

13. The method of claim 12, wherein said composition comprises yogurt or a probiotic beverage.

14. The method of claim 12, wherein said composition comprises a weaning food.

15. The method of claim 12, wherein said mammalian subject is not an infant.

16. The method of claim 15, wherein said mammalian subject is a child.

17. The method of claim 15, wherein said mammalian subject is an adult.

18. The method of claim 12, wherein said mammalian subject is afflicted with infectious diarrhea, antibiotic-associated diarrhea, traveler's diarrhea, necrotizing enterocolitis, or a *Helicobacter pylori* infection.

19. The method of claim 12, wherein said mammalian subject is afflicted with inflammatory bowel disease.

20. The method of claim 12, wherein said composition comprises 2'-FL.

21. The method of claim 1, wherein the *Bacteroides* sp. bacterium is derived from healthy human microflora.

22. The method of claim 1, wherein said oligosaccharides stimulate the growth of an endogenous *Bacteroides* sp. bacterium present in human intestinal microflora.

23. A method for stimulating the growth of an exogenously administered probiotic bacterium in a gastrointestinal tract of a mammalian subject, comprising:
    administering to said subject a composition comprising an oligosaccharide, wherein said oligosaccharide comprises (a) purified 2'-fucosyllactose (2'-FL), (b) purified 3-fucosyllactose(3-FL), (c) purified lactodifucotetraose (LDFT), or (d) a combination thereof, wherein the composition further comprises a probiotic *Bacteroides* sp. bacterium, wherein said oligosaccharide selectively stimulates the growth of said probiotic *Bacteroides* sp. bacterium, and wherein the *Bacteroides* sp. bacterium is a *Bacteroides fragilis, Bacteroides thetaiotaomicron*, or *Bacteroides vulgatus* bacterium.

* * * * *